United States Patent
Kim et al.

(10) Patent No.: US 6,329,472 B1
(45) Date of Patent: Dec. 11, 2001

(54) WATER-SOLUBLE OR WATER-DISPERSIBLE GRAFT COPOLYMERS BASED ON A POLYVINYLLACTAM, THEIR PREPARATION AND USE

(75) Inventors: Son Nguyen Kim, Hemsbach; Axel Sanner, Frankenthal; Peter Hössel; Volker Schehlmann, both of Schifferstadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/441,092

(22) Filed: Nov. 16, 1999

(30) Foreign Application Priority Data

Nov. 18, 1998 (DE) .............................................. 198 53 046

(51) Int. Cl.$^7$ ................ C08F 26/06; A61K 7/06
(52) U.S. Cl. ................ 525/326.9; 526/264; 424/70.1; 424/70.11; 424/70.16
(58) Field of Search ................ 525/326.9; 424/70.1, 424/70.11, 70.16

(56) References Cited

U.S. PATENT DOCUMENTS

| | | | |
|---|---|---|---|
| 3,301,808 | 1/1967 | Mack et al. | 260/29.6 |
| 3,405,084 | 10/1968 | Bohac | 260/29 |
| 3,594,344 | 7/1971 | Barabas et al. | 260/29 |
| 3,770,683 | 11/1973 | Barabas et al. | 260/29 |
| 4,767,613 | * 8/1988 | Nuber et al. | 424/71 |
| 5,730,966 | * 3/1998 | Torgerson et al. | 424/70.11 |

FOREIGN PATENT DOCUMENTS

| | | |
|---|---|---|
| 4202193 | 7/1993 | (DE) . |
| 257444 | 3/1988 | (EP) . |

\* cited by examiner

*Primary Examiner*—James J. Seidleck
*Assistant Examiner*—Olga Asinovsky
(74) *Attorney, Agent, or Firm*—Keil & Weinkauf

(57) ABSTRACT

Water-soluble or water-dispersible graft copolymers in which a tert-butyl acrylate and a polymerizable carboxylic acid are grafted onto a polyvinyllactam, to their preparation and to their use, especially in the form of cosmetic preparations, particularly as hair-setting compositions.

12 Claims, No Drawings

WATER-SOLUBLE OR WATER-DISPERSIBLE GRAFT COPOLYMERS BASED ON A POLYVINYLLACTAM, THEIR PREPARATION AND USE

Water-soluble or water-dispersible graft copolymers based on a polyvinyllactam, their preparation and use The invention relates to graft copolymers in which a tert-butyl acrylate and a polymerizable carboxylic acid are grafted onto a polyvinyllactam, to their preparation and to their use, especially in the form of cosmetic preparations, particularly as hair-setting compositions.

A large number of substances have already been described as film formers for cosmetic preparations, in particular for hair cosmetics. The majority are synthetically obtained polymers which are applied to the hair in dissolved form by rubbing in or spraying onto the hair, where they leave behind a transparent colorless film after the solvent has evaporated.

A number of requirements are placed on such substances: the film should adhere firmly to the hair and not flake off or dust off. It should be clear, impart gloss and not be sensitive to moisture so that the treated hairstyle retains its shape, does not stick and bind dust even at high atmospheric humidity. On the other hand, it should be possible to wash out the polymer using a standard commercial shampoo without leaving a residue. Finally, the sprayability of the film former solution requires sufficient solubility of the polymer in the solvents customary for hair treatment compositions and, in the case of application as a spray from a pressurized pack, the problem-free miscibility of the solution with the propellants.

While initially vinyllactam homo- and copolymers were preferentially used, carboxylate-containing polymers have later become increasingly important. The desired profile of properties such as strong hold at high atmospheric humidity, elasticity, wash-off from the hair and compatibility with the other formulation components is achieved by copolymerization of a combination of hydrophobic, elastifying and carboxyl-containing monomers.

Although the above requirements are nowadays achieved by various types of polymer, the feel of hairstyles held using these polymers is being perceived more and more frequently as unpleasantly dull and unnatural. Attempts to achieve an improvement by making additions to the formulations have hitherto led to results which are not entirely satisfactory: although the addition of customary plasticizers does improve the feel, it at the same time reduces the setting action in many cases. The frequently used polysiloxanes are incompatible with the polar polymers and often require further additives in order that they can be formulated at all. Separation out of individual components can lead to problems both during storage of the formulation and during use.

This is true, for example, for the terpolymers described in U.S. Pat. No. 3,405,084, which comprise from 25 to 75% of vinylpyrrolidone, from 20 to 70% of acrylate and from 3 to 25% of acrylic acid.

Improved terpolymers according to EP-A 0 257 444 comprise from 20 to 50% of vinylpyrrolidone, from 40 to 70% of tert-butyl acrylate and from 2 to 15% of acrylic acid or methacrylic acid.

In addition, U.S. Pat. No. 3,594,344 describes graft copolymers for hairspray formulations which have been prepared by grafting a monomer mixture of alkyl acrylates and at least 1% by weight of glycidyl methacrylate onto polymeric N-vinyllactam. A disadvantage of these polymers is, however, not only the toxicity of the glycidyl methacrylate, but also the high crosslinking tendency of this bifunctional monomer. This can lead, for example, to storage instability of the dispersion. Moreover, the epoxide groups of the polymer can form a permanent chemical bond with the proteinaceous substance of the hair and of the scalp. Such polymers cannot be washed out and are rejected as physiologically objectionable.

U.S. Pat. No. 3,770,683 describes emulsion graft copolymers for hairspray formulations which have been prepared by grafting a monomer mixture of (meth)acrylic esters and at least 0.5% by weight of an ethylenically unsaturated monocarboxylic acid onto polymeric N-vinyllactam.

There has then been no lack of attempts to improve the properties of these polymers such that they are less sensitive to moisture and can be used especially in regions with a hot humid climate.

Accordingly, it has already been proposed, according to DE-A 42 02 193, to use emulsion graft copolymers of polyvinyllactams with grafted-on acrylic esters for hair cosmetics. In this connection, it has been found that it is not advantageous to copolymerize monomers containing carboxylic groups, as is described in U.S. Pat. No. 3,770,683, since the neutralization or partial neutralization required for solubility in water does not leave many options, meaning that films are readily obtained which are either difficult to wash out or are soft and sensitive to moisture.

It is an object of the present invention to propose further improved graft polymers which are neither sensitive to moisture nor leave, as a result of their hardness, a flaky residue on the hair when combed out, and which can also be used in a hot and humid climate.

We have found that this object is achieved according to the invention by particular graft polymers, the content of carboxyl-containing comonomers surprisingly not leading to the disadvantages described in DE-A 42 02 193.

Accordingly, the invention provides water-soluble or water-dispersible graft copolymers with a K value of from 30 to 70, obtainable by free-radical polymerization of monomers (A) consisting essentially of
  (a) from 50 to 85% by weight of monomers of the formula I

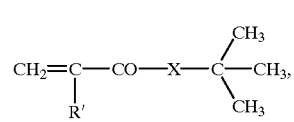

in which R' is hydrogen or $C_1$- to $C_6$-alkyl radicals, and X is the radical

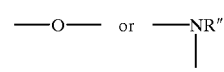

where R" is hydrogen or a $C_1$- to $C_6$-alkyl radical, and
  (b) from 15 to 30% by weight of a vinyl monomer which has at least one carboxyl group, and, where appropriate,
  (c) from 0 to 25% by weight of a free-radically polymerizable vinyl monomer of the formula II

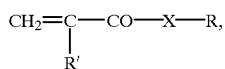

in which R is a $C_6$–$C_{30}$-alkyl radical, preferably $C_6$–$C_{22}$-alkyl radical, and R' and X are as defined above, with B) a prepolymer with a K value of from 30 to 50, comprising, in copolymerized form, at least 30% by weight of monomers of the formula III

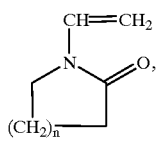

in which n is a number from 1 to 3,
the weight ratio A:B being from 100:5 to 100:200, and at least partial neutralization of the graft copolymer.

Component A(a) is preferably an α,β-ethylenically unsaturated compound of the formula I in which R' is hydrogen, methyl or ethyl, and X is O or NR", where R" is hydrogen, methyl, ethyl, n-propyl, isopropyl, n-butyl, sec-butyl, tert-butyl or cyclohexyl.

In this connection, it is also possible to use mixtures of compounds of component A(a).

Component A(a) is preferably tert-butyl acrylate, tert-butyl methacrylate, tert-butyl ethacrylate, N-tert-butylacrylamide, N-tert-butylmethacrylamide, N-tert-butylethacrylamide, and mixtures thereof.

Tert-butyl methacrylate is preferable and tert-butyl acrylate is particularly preferable.

Monomers (A)(b) are any, in particular low molecular weight compounds which contain one or more carboxyl-carrying vinyl groups. Specific examples which may be given are acrylic acid, methacrylic acid, fumaric acid, maleic acid, itaconic acid, crotonic acid and mixtures thereof. Preference is given to acrylic acid, methacrylic acid and mixtures thereof.

Suitable monomers (A)(c) of the formula II are, preferably, those in which R' is hydrogen, methyl or ethyl, X=O or NH, and R is the radicals n-octyl, ethylhexyl, 1,1,3,3-tetramethylbutyl, undecyl, lauryl, tridecyl, myristyl, pentadecyl, palmityl, margarinyl, stearyl, palmitoleinyl, oleyl or linolyl.

The component (A)(c) is chosen in particular from n-octyl (meth)acrylate, 1,1,3,3-tetramethylbutyl (meth)acrylate, ethylhexyl (meth)acrylate, n-nonyl (meth)acrylate, n-decyl (meth)acrylate, n-undecyl (meth)acrylate, tridecyl (meth) acrylate, myristyl (meth)acrylate, pentadecyl (meth) acrylate, palmityl (meth)acrylate, heptadecyl (meth) acrylate, nonadecyl (meth)acrylate, arrachinyl (meth) acrylate, behenyl (meth)acrylate, lignocerenyl (meth) acrylate, cerotinyl (meth)acrylate, melissinyl (meth) acrylate, palmitoleinyl (meth)acrylate, oleyl (meth)acrylate, linolyl (meth)acrylate, linolenyl (meth)acrylate, stearyl (meth)acrylate, lauryl (meth)acrylate, n-octyl(meth) acrylamide, 1,1,3,3-tetramethylbutyl(meth)acrylamide, ethylhexyl(meth)acrylamide, n-nonyl(meth)acrylamide, n-decyl(meth)acrylamide, n-undecyl(meth)acrylamide, tridecyl(meth)acrylamide, myristyl(meth)acrylamide, pentadecyl(meth)acrylamide, palmityl(meth)acrylamide, heptadecyl(meth)acrylamide, nonadecyl(meth)acrylamide, arrachinyl(meth)acrylamide, behenyl(meth)acrylamide, lignocerenyl(meth)acrylamide, cerotinyl(meth)acrylamide, melissinyl(meth)acrylamide, palmitoleinyl(meth) acrylamide, oleyl(meth)acrylamide, linolyl(meth) acrylamide, linolenyl(meth)acrylamide, stearyl(meth) acrylamide, lauryl(meth)acrylamide and mixtures thereof.

In particular, stearyl(meth)acrylamide, lauryl (meth) acrylate, stearyl (meth)acrylate and, preferably, stearyl acrylate are to be mentioned.

The starting prepolymer (B) comprises at least 30% by weight of a vinyllactam, preferably vinylpyrrolidone or vinylcaprolactam. Examples are pure polyvinylpyrrolidone or polyvinylcaprolactam or mixtures thereof or copolymers which comprise, in copolymerized form, vinylpyrrolidone and/or vinylcaprolactam in any weight ratio.

Corresponding copolymers comprise, as further comonomers, preferably an ester or else amides of (meth) acrylic acid (M1) and/or a tert-amine-containing monomer (M2), it being possible for the content of M1 to be up to 50% by weight and the content of M2 to be up to 20% by weight.

The prepolymer (B) is either a homopolymer of vinylcaprolactam or vinylpyrrolidone, a copolymer of vinylcaprolactam and vinylpyrrolidone or a copolymer of vinylcaprolactam and/or vinylpyrrolidone with a $C_1$–$C_{30}$-alkyl ester or alkylamide of acrylic or methacrylic acid (M1) and/or a tert-amine-containing monomer (M2) of the formula V

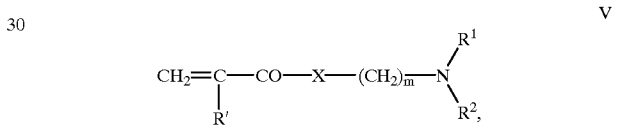

in which R' is hydrogen or a $C_1$- to $C_6$-alkyl radical, preferably hydrogen or methyl, $R^1$ and $R^2$ independently of one another are an alkyl radical having from 1 to 6 carbon atoms, preferably methyl, X is oxygen or an imino group, and m is a number from 2 to 8, preferably 2 or 3.

Preferred monomers of the formula V are dimethylaminoethyl acrylate, dimethylaminoethyl methacrylate, dimethylaminopropyl acrylate, dimethylaminopropyl methacrylate, dimethylaminoethylacrylamide, dimethylaminoethylmethacrylamide, dimethylaminopropylacrylamide, dimethylaminopropylmethacrylamide.

Preferred copolymers of vinylpyrrolidone with a $C_1$–$C_{30}$-alkyl acrylate are copolymers with tert-butyl acrylate.

The weight ratio of the monomers (A) to be grafted on to the prepolymer (B) is from 100:5 to 100:200, preferably from 100:10 to 100:100 and in particular from 100:20 to 100:70.

The graft copolymers according to the invention are prepared in a manner known per se by free-radically initiated suspension, emulsion and, preferably, solution polymerization by grafting the monomers (A) onto the prepolymer (B). In this connection, it is also possible for some of the grafted-on monomer component to be present in the resulting graft copolymer as isolated polymer chains without grafting having taken place.

The initiators used for the free-radical polymerization reaction are the customary peroxo or azo compounds, for example dibenzoyl peroxide, tert-butyl perpivalate, tert-butyl per-2-ethylhexanoate, di-tert-butyl peroxide, tert-butyl hydroperoxide, 2,5-dimethyl-2,5-di(tert-butylperoxy) hexane, alkali metal or ammonium persulfates, azobisbutyronitrile, hydrogen peroxide or redox initiators advantageously in amounts of from 0.1 to 2% by weight, based on the weight of the monomers. The amount of monomers and solvents or dispersants is advantageously chosen to give 30- to 80% strength by weight solutions of the copolymers. To reduce the residual monomer content, it is possible to carry out an afterpolymerization by generally known processes.

The copolymers should have K values of from 25 to 60, preferably from 30 to 50. The K value desired in each case can be set in a manner known per se by appropriate choice of the polymerization conditions, for example the polymerization temperature and the initiator concentration. If appropriate, it is also possible to use regulators, in particular sulfur compounds such as mercaptoethanol, 2-ethylhexyl thioglycolate, thioglycolic acid or dodecylmercaptan to reduce the K value. The K values are measured according to Fikentscher, Cellulosechemie, Vol. 13, p. 58 to 64 (1932) at 25° C. in 1% strength by weight ethanolic solution, and are a measure of the molecular weight.

Such copolymers usually have glass transition temperatures from 50 to 130° C., in particular from 60 to 100° C.

Suitable emulsifiers and protective colloids, which mainly serve as dispersants, are, in particular, anionic surfactants such as the alkali metal salts of fatty acids (soaps) or the alkali metal salts of alkyl sulfates, e.g. sodium lauryl sulfate, but nonionic and cationic emulsifiers or protective colloids, e.g. polyethylene oxides, polyoxyethylene-polyoxypropylene block copolymers and quaternary ammonium salts such as cetyltrimethylammonium bromide, can also be used.

Furthermore, it is also possible to add to the reaction mixture other customary auxiliaries, such as, for example, buffer substances, complexing agents or electrolyte additions to further reduce the viscosity.

The resulting aqueous dispersions are partially neutralized or completely neutralized depending on the content of monomers (A)(b) in order to render the graft copolymers soluble in water or at least dispersible in water. The extent of neutralization can be readily established in individual cases from the result of the solubility in water or dispersibility in water. For the neutralization, alkali metal bases or alkaline earth metal bases or amines are normally used.

The neutralization is preferably carried out with a mono-, di- or trialkanolamine having from 2 to 5 carbon atoms in the alkanol radical, which is optionally in etherified form, for example mono-, di- and triethanolamine, mono-, di- and tri-n-propanolamine, mono-, di- and triisopropanolamine, 2-amino-2-methylpropanol and di(2-methoxyethyl)amine, an alkanediolamine having from 2 to 5 carbon atoms, for example 2-amino-2-methylpropane-1,3-diol and 2-amino-2-ethylpropane-1,3-diol, or a primary, secondary or tertiary alkylamine having a total of from 5 to 10 carbon atoms, for example N,N-diethylpropylamine.

Particularly good results were obtained with 2-amino-2-methylpropanol, triisopropanolamine and 2-amino-2-ethylpropane-1,3-diol.

Alkali metal hydroxides which are suitable for the neutralization are, in particular, sodium and potassium hydroxides.

The graft copolymers according to the invention are excellent film formers in hair cosmetic preparations, especially in hair-setting compositions such as hairsprays, aqueous hair-setting lotions, hair gels or hair mousses. They can be applied to the hair without further additions of bases and hydrophobicizing agents, hold the hair elastically, impart gloss thereto, adhere well, bring about neither hygroscopicity nor sensitivity to moisture, exhibit reduced tack at high atmospheric humidity and can be removed from the hair without problems using standard commercial shampoos.

Corresponding hair cosmetic preparations normally comprise from 0.1 to 20% by weight, preferably from 0.5 to 10% by weight, and in particular from 2 to 10% by weight, of the partially or completely neutralized novel graft copolymers in addition to customary solvents, such as water and/or alcohols, and also, where appropriate, propellants, e.g.

from 1 to 99.9% by weight, preferably from 5 to 50% by weight, in particular from 10 to 40% by weight, of water, from 0 to 95% by weight, preferably from 20 to 60% by weight, in particular from 25 to 50% by weight, of a customary organic solvent, such as, in particular, ethanol, isopropanol and dimethoxymethane and also acetone, n-propanol, n-butanol, 2-methoxypropan-1-ol, n-pentane, n-hexane, cyclohexane, n-heptane, n-octane or dichloromethane or mixtures thereof, from 0 to 90% by weight, preferably from 30 to 80% by weight, in particular from 45 to 70% by weight, of a customary propellant such as propane, n-butane, isobutane, 2,2-dimethylbutane, n-pentane, isopentane, dimethyl ether, difluoroethane, fluorotrichloromethane, dichlorodifluoromethane or dichlorotetrafluoroethane or mixtures thereof.

The hair setting compositions can additionally comprise from 0 to 10% by weight of a standard commercial hair polymer, from 0 to 0.5% by weight of a water-soluble or dispersible silicone compound, and from 0 to 0.2% by weight of customary additives.

The graft polymers according to the invention can also be used in combination with other hair polymers e.g. from 0 to 10% by weight of a standard commercial hair polymer. Such polymers are, in particular:

nonionic, water-soluble or water-dispersible polymers or oligomers, such as polyvinylcaprolactam, e.g. Luviskol Plus (BASF), or polyvinylpyrrolidone and copolymers thereof, in particular with vinyl esters, such as vinyl acetate, e.g. Luviskol VA 37 (BASF); polyamides, e.g. based on itaconic acid and aliphatic diamines;

amphoteric or zwitterionic polymers, and the octylacrylamide-methyl methacrylate-tert-butylaminoethyl methacrylate-2-hydroxypropyl methacrylate copolymers available under the name Amphomer® (Delft National), and zwitterionic polymers, such as those disclosed, for example, in German patent applications DE 39 29 973, DE 21 50 557, DE 28 17 369 and DE 37 08 451. Acrylamidopropyltrimethylammonium chloride-acrylic or -methacrylic acid copolymers and the alkali metal and ammonium salts thereof are preferred zwitterionic polymers. Other suitable zwitterionic polymers are methacrylethylbetain-methacrylate copolymers, which are available commercially under the name Amersette® (AMERCHOL), and copolymers of hydroxyethyl methacrylate, methyl methacrylate, N,N-dimethylaminoethyl methacrylate and acrylic acid (Jordapon®);

anionic polymers, such as vinyl acetate-crotonic acid copolymers, available commercially for example under the names Resyn® (NATIONAL STARCH), Luviset® (BASF) and Gafset® (GAF), vinylpyrrolidone-vinyl acrylate copolymers, obtainable for example under the tradename Luviflex® (BASF). A preferred polymer is the vinylpyrrolidone-acrylate terpolymer obtainable under the name Luviflex® VBM-35 (BASF), acrylic acid-ethyl acrylate-N-tert-butylacrylamide terpolymers, which are sold, for example, under the name Ultrahold® strong (BASF), and Luvimer® (BASF, terpolymer comprising t-butyl acrylate, ethyl acrylate and methacrylic acid), or anionic polyurethanes as known, for example, from DE-A 4 225 045 and EP-A 619 111 or silicone-containing polyurethanes as known from EP-A 636 361;

cationic (quaternized) polymers, e.g. cationic polyacrylate copolymers based on N-vinyllactams and derivatives thereof (N-vinylpyrrolidone, N-vinylcaprolactam etc.), and customary cationic hair conditioning polymers, e.g. Luviquat® (copolymer of vinylpyrrolidone and vinylimidazolium methochloride), Luviquat® Hold (copolymer of quaternized N-vinylimidazol, N-vinylpyrrolidone and N-vinylcaprolactam), Merquat® (polymer based on dimethyldiallylammonium chloride), Gafquat® (quaternary polymers which are formed by reaction of polyvinylpyrrolidone with quaternary ammonium compounds), polymer JR (hydroxyethylcellulose with cationic groups), polyquaternium products (CTFA names) etc.;

nonionic siloxane-containing, water-soluble or -dispersible polymers, e.g. polyether siloxanes, such as Tegopren® (Goldschmidt) or Belsil® (Wacker).

In addition, the hair treatment compositions according to the invention generally comprise customary cosmetic auxiliaries, for example plasticizers, such as glycerol and glycol; emollients; perfumes; UV adsorbers; dyes; antistatics; agents for improving combability; preservatives; and antifoams.

From the compounds mentioned, especially suitable propellants 30 (propellant gases) are the hydrocarbons, in particular propane, n-butane, n-pentane and mixtures thereof, and dimethyl ether and trifluoroethane. Where appropriate, one or more of said chlorinated hydrocarbons are co-used in propellant mixtures, but only in small amounts, for example up to about 20% by weight, based on the propellant mixture.

Accordingly, a hair-setting preparation according to the invention comprises, for example, from 0.5 to 20% by weight of a graft copolymer according to the invention, from 0 to 10% by weight of a standard commercial hair polymer, from 50 to 99.5% by weight of an alcohol and/or water as solvent, from 0 to 50% by weight of a propellant in the form of propane/butane and/or dimethyl ether, from 0 to 0.5% by weight of a water-soluble or dispersible silicone compound and from 0 to 0.2% by weight of customary additives.

The hair-setting compositions according to the invention are also particularly suitable for pump spray preparations without the addition of propellants or else for aerosol sprays with customary compressed gases such as nitrogen, compressed air or carbon dioxide as propellant.

In addition, these spray preparations can also comprise small amounts of perfume oils, for example from 0.1 to 0.5% by weight.

A hydrous standard spray formulation has, for example, the following composition:

from 2 to 10% by weight of the graft copolymer neutralized to 100% with 2-amino-2-methylpropanol, from 10 to 76% by weight of ethanol, from 2 to 40% by weight of water, from 10 to 40% by weight of dimethyl ether.

The graft copolymers present in hair-setting compositions according to the invention are notable for their high compatibility with the nonpolar propellants in spray preparations, in particular with hydrocarbons such as propane or n-butane, or a mixture thereof. They display good hair-setting action, evident from the high values for curl retention, which in most cases are above 80%. In addition, the hair-setting compositions according to the invention are notable for the fact that they virtually prevent the hair from sticking together.

However, the main advantage of the hair-setting compositions according to the invention is that they exhibit excellent results for the application properties which were referred to at the outset as in need of improvement in the case of prior art compositions. They dissolve in alcohols such as ethanol or isopropanol or in mixtures of these alcohols with water to give clear solutions. The clarity of the solutions is also retained when the solutions are used in standard spray formulations together with propellants such as dimethyl ether. The hair-setting compositions according to the invention can be washed out of the hair without problems. Hair treated with them has increased smoothness and a pleasant natural feel. The setting action is also good, making it possible, in principle, to reduce the required amount of film former in the hairspray formulation.

The graft copolymers according to the invention are also suitable as coatings or binders in pharmaceutical preparations.

EXAMPLES

Example 1 a) Preparation of the prepolymer

| Initial charge: | 65.0 g of ethanol |
| | 32.0 g of the total amount of Feed 1 |
| | 10.0 g of the total amount of Feed 2 |
| Feed 1: | 150 g of vinylcaprolactam (Vcap) |
| Feed 2: | 80.0 g of ethanol |
| | 0.4 g of t-butyl perpivalate |
| Feed 3: | 80.0 g of ethanol |
| | 1.6 g of t-butyl perpivalate |

The initial charge of mixture was heated to 80° C. under nitrogen with stirring in a stirred apparatus with 3 feed units. The feeds were then started and Feed 1 was metered in over the course of 3 hours, and Feed 2 was metered in over the course of 4 hours. After the mixture had been polymerized for a further 5 hours at 80° C., Feed 3 was started and metered in over the course of 1 hour. Renewed polymerization for a further 5 hours gave a 40% strength ethanolic polyvinylcaprolactam solution.

A similar method was used to prepare the prepolymers B2 to B4 in Table 1:

TABLE 1

| Prepolymer | Vcap % by weight | VP % by weight | DMAPMA % by weight | TBA % by weight |
|---|---|---|---|---|
| B2 | 50 | 50 | — | — |
| B3 | 35 | 35 | 30 | — |
| B4 | — | 65 | — | 35 |

VP: vinylpyrrolidone
Vcap: vinylcaprolactam
DMAPMA: dimethylaminopropylmethacrylamide
TBA: tert-butyl acrylate b) Preparation of the graft polymers

| | |
|---|---|
| Initial charge: | 32.0 g of the total amount of Feed 1 |
| | 10.0 g of the total amount of Feed 2 |
| | 375.0 g (40% strength in ethanol) of solution B1. |
| Feed 1: | 60.0 g of MAS |
| | 240.0 g of TBA |
| Feed 2: | 100.0 g of ethanol |
| | 0.4 g of t-butyl perpivalate |
| Feed 3: | 150.0 g of ethanol |
| | 1.6 g of t-butyl perpivalate |
| Feed 4: | 200.0 g of ethanol |

The initial charge of mixture was heated to 80° C. under nitrogen with stirring in a stirred apparatus with 4 feed units. Feeds 1 and 2 were then started and Feed 1 was metered in over the course of 3 hours, and Feed 2 was metered in over the course of 4 hours. After the mixture had been afterpolymerized for 5 hours at 80° C., Feed 3 was started and metered in over the course of 1 hour and the mixture was polymerized at 80° C. for a further 5 hours. The mixture was cooled and during cooling diluted with Feed 4 to give an ethanolic polymer solution which can be used directly for the preparation of hair cosmetics.

The same procedure was used to obtain the graft copolymers of Examples 2 to 8 as shown in Table 2 below.

TABLE 2

| | (A) | | | (A):(B) | DN | K value | | Hold | Film | |
|---|---|---|---|---|---|---|---|---|---|---|
| Example | TBA | MAS | SMA | TI:TI | with AMP | in EtOH | CR % | grade | clarity | Wash-off |
| 1 | 80 | 20 | — | (A):(B1) 100:50 | 95 | 37.7 | 84 | 2 | clear | good |
| 2 | 80 | 20 | — | (A):(B2) 100:50 | 95 | 39.2 | 83 | 2 | clear | very good |
| 3 | 80 | 20 | — | (A):(B3) 100:50 | 95 | 42 | 76.3 | 1–2 | clear | very good |
| 4 | 78 | 22 | — | (A):(B4) 100:50 | 90 | 38.6 | 80 | 2 | almost clear | good |
| 5 | 68 | 22 | 10 | (A):(B1) 100:35 | 95 | 42 | 81 | 2 | clear | good |
| 6 | 68 | 22 | 10 | (A):(B2) 100:35 | 95 | 39.8 | 79.4 | 1–2 | clear | very good |
| 7 | 68 | 22 | 10 | (A):(B3) 100:35 | 95 | 40.3 | 77 | 1–2 | clear | very good |
| 8 | 66 | 24 | 10 | (A):(B4) 100:35 | 95 | 38.7 | 81 | 2 | clear | very good |

TBA: tert-butyl acrylate
MAS: methacrylic acid
SMA: stearin methacrylate
AMP: aminomethylpropanol
DN: degree of neutralization
CR: curl retention
Grade: 1/2/3/4 = very good/good/acceptable/poor

Example 9 (Comparison)

In accordance with the details of Example 1 (b), a polymer (without an initial charge of prepolymer) was prepared, the properties of which are given in Table 3.

TABLE 3

| | (A) | | | (A):(B) | DN | K value | | Hold | Film | |
|---|---|---|---|---|---|---|---|---|---|---|
| Polymer | TBA | MAS | SMA | TI:TI | with AMP | in EtOH | CR % | grade | clarity | Wash off |
| 9 | 80 | 20 | — | (A):(B) 100:0 | 95 | 40.7 | 84 | 1–2 | clear | poor |

For comparison, this polymer 9, pure prepolymer B1 and the mixture of the two were investigated and rated in Table 4:

TABLE 4

| | Polymer No. 9 | Polymer No. B1 | Film |
|---|---|---|---|
| 1 | 100 parts | 0 part | clear; smooth |
| 2 | 0 | 100 | clear; smooth |

TABLE 4-continued

|   | Polymer No. 9 | Polymer No. B1 | Film |
|---|---|---|---|
| 3 Mixture instead of graft polymer; for comparison | 100 parts | 50 parts | cloudy; matt => incompatibility |

EXAMPLES 10 to 13

(use as hair-setting composition)

Example 10

| Aerosol hairspray | [%] |
|---|---|
| Polymer No. 1–8 | 3.00 |
| Dimethyl ether | 50.00 |
| Ethanol | 47.00 |
| Other additives silicone, perfume, antifoam etc. | |

Example 11

| Aerosol hairspray | [%] |
|---|---|
| Polymer No. 1–8 | 5.00 |
| Propane/butane gas | 50.00 |
| Ethanol | 45.00 |
| Other additives silicone, perfume, antifoam etc. | |

Example 12

| VOC 80 aerosol-hairspray | [%] |
|---|---|
| Polymer No. 1–8 | 5.00 |
| Water | 15.00 |
| Dimethylether | 40.00 |
| Ethanol | 40.00 |
| Other additives silicone, perfume, antifoam etc. | |

Example 13

| VOC 55 handpump spray | [%] |
|---|---|
| Polymer No. 1–8 | 5.00 |
| Water | 40.00 |
| Ethanol | 55.00 |
| Other additives silicone, perfume, antifoam etc. | |

(VOC = volatile organic compounds in percent)

We claim:

1. A water-soluble or water-dispersible graft copolymer with a K value of from 30 to 70, obtained by free-radical polymerization of monomers
   (A) consisting essentially of
      (a) from 50 to 85% by weight of monomers of the formula I

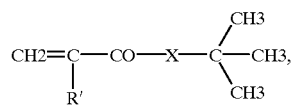

in which R' is hydrogen or a $C_1$- to $C_6$-alkyl radical, and X is the radical

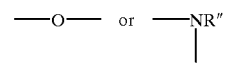

where R'' is hydrogen or a $C_1$- to $C_6$-alkyl radical, and
      (b) from 15 to 30% by weight of a vinyl monomer which has at least one carboxyl group, and,
      (c) from 0 to 25% by weight of a free-radically polymerizable vinyl monomer of the formula II

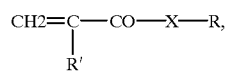

in which R is a $C_6$- to $C_{30}$-alkyl radical, and R' and X are as defined above, with
   (B) a prepolymer with a K value of from 30 to 50, comprising, in copolymerized form, at least 30% by weight of monomers of the formula III

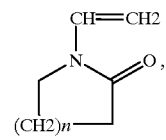

in which n is number from 1 to 3, the weight ratio A:B being from 100:5 to 100:200, and at least partial neutralization of the graft copolymer.

2. A water-soluble or water-dispersible graft copolymer as claimed in claim 1, wherein the monomers
   (A) consist, in an amount of
      (a) from 65 to 85% by weight, of tert-butyl acrylate,
      (b) from 15 to 25% by weight, of methacrylic acid and
      (c) from 0 to 10% by weight, of stearyl methacrylate, and are polymerized onto a prepolymer
   (B) of the formula IV

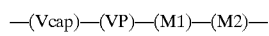

where Vcap is vinylcaprolactam, VP is vinylpyrrolidone, M1 is an ester of methacrylic acid or acrylic acid with a $C_1$- to $C_{30}$-alcohol, or a $C_1$–$C_{30}$-alkylamide of methacrylic acid or acrylic acid, and M2 is a tert-amine-containing monomer, where the content a of Vcap is from 0 to 100% by weight, of VP is from 0 to 100% by weight, of M1 is from 0 to 50% by weight, and of M2 is from 0 to 20% by weight, with the proviso that the sum of Vcap and VP is at least 30% by weight, and the mass ratio (A) to (B) is from 100:20 to 100:70.

3. A water-soluble or water-dispersible graft copolymer as claimed in claim 1, wherein the prepolymer (B) is polyvinylcaprolactam.

4. A water-soluble or water-dispersible graft copolymer as claimed in claim 1, wherein the prepolymer (B) is polyvinylpyrrolidone.

5. A water-soluble or water-dispersible graft copolymer as claimed in claim 1, wherein the prepolymer (B) is a copolymer of vinylpyrrolidone and vinylcaprolactam.

6. A water-soluble or water-dispersible graft copolymer as claimed in claim 1, wherein the prepolymer (B) is a copolymer of vinylpyrrolidone and/or vinylcaprolactam and a monomer which contains a tertiary amine group.

7. A water-soluble or water-dispersible graft copolymer as claimed in claim 6, wherein the monomer which contains a tertiary amine group is a monomer of the formula V

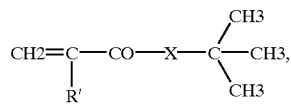

in which R' is hydrogen or a $C_1$- to $C_6$-alkyl radical, X is oxygen or an imino group, m is a number from 2 to 8, and $R^1$ and $R^2$ independently of one another are an alkyl radical having from 1 to 6 carbon atoms.

8. A process for the preparation of graft copolymers as claimed in claim 1, which comprises free-radically polymerizing the monomers (A), consisting of
(a) from 50 to 85% by weight of monomers of the formula I

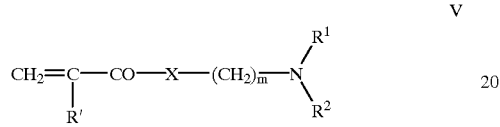

in which R' is hydrogen or a $C_1$- to $C_6$-alkyl radical, and X is the radical

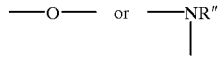

where R" is hydrogen or a $C_1$- to $C_6$-alkyl radical, and (b) from 15 to 30% by weight of a vinyl monomer which has at least one carboxyl group, and, (c) from 0 to 25% by weight of a free-radically polymerizable vinyl monomer of the formula II

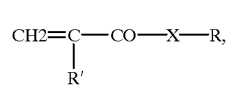

in which R is a $C_6$- to $C_{30}$-alkyl radical, and R' and X are as defined above, with (B) a prepolymer with a K value of from 30 to 50, comprising, in copolymerized form, at least 30% by weight of monomers of the formula III

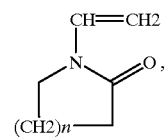

in which n is a number from 1 to 3, the weight ratio A:B being from 100:5 to 100:200, and at least partial neutralization of the graft copolymer.

9. A process for making cosmetic preparations comprising the step of incorporating the water soluble graft copolymer as claimed in claim 1 as a constituent.

10. A hair cosmetic preparation comprising from 0.5 to 20% by weight of a graft copolymer as claimed in any of claim 1.

11. A process for preparing a coating or binder in pharmaceutical preparations comprising the step of incorporating the water soluble graft copolymer as claimed in claim 1 as a constituent.

12. A hair-setting preparation comprising
from 0.5 to 20% by weight of a graft copolymer as claimed in any of claims 1,
from 0 to 10% by weight of a standard commercial hair polymer,
from 50 to 99.5% by weight of an alcohol and/or water as solvent,
from 0 to 50% by weight of a propellant in the form of propane/butane and/or dimethyl ether,
from 0 to 0.5% by weight of a water-soluble or dispersible silicone compound and
from 0 to 0.2% by weight of customary additives.

* * * * *